(12) United States Patent
Oliver et al.

(10) Patent No.: US 12,343,534 B2
(45) Date of Patent: Jul. 1, 2025

(54) TINNITUS TREATMENT AND ANALYSIS

(71) Applicant: University of Connecticut, Farmington, CT (US)

(72) Inventors: Douglas L. Oliver, West Hartford, CT (US); Alice L. Burghard, Wolcott, CT (US); Christopher Lee, West Hartford, CT (US); Emily Fabrizio-Stover, Rocky Hill, CT (US)

(73) Assignee: University of Connecticut, Farmington, CT (US)

( * ) Notice: Subject to any disclaimer, the term of this patent is extended or adjusted under 35 U.S.C. 154(b) by 572 days.

(21) Appl. No.: 17/554,973

(22) Filed: Dec. 17, 2021

(65) Prior Publication Data

US 2022/0193411 A1    Jun. 23, 2022

Related U.S. Application Data (60) Provisional application No. 63/127,275, filed on Dec. 18, 2020.

(51) Int. Cl.
*A61N 1/36* (2006.01)
*A61B 5/00* (2006.01)
(Continued)

(52) U.S. Cl.
CPC .......... *A61N 1/36036* (2017.08); *A61B 5/123* (2013.01); *A61B 5/128* (2013.01);
(Continued)

(58) Field of Classification Search
CPC .. A61N 1/0456; A61N 1/36036; H04R 25/75; A61B 5/123; A61B 5/128; A61B 5/4836; A61B 5/7228; A61B 5/7235
See application file for complete search history.

(56) References Cited

U.S. PATENT DOCUMENTS 6,631,295 B2    10/2003    Rubinstein et al.
8,088,077 B2    1/2012    Turner et al.
(Continued)

FOREIGN PATENT DOCUMENTS

CN    1090159 A    8/1994
CN    1663528 A    9/2005
(Continued)

OTHER PUBLICATIONS

Adjamian, P. et al., "Neuromagnetic Indicators of Tinnitus and Tinnitus Masking in Patients with and without Hearing Loss," JARO, 2012, pp. 715-731, vol. 13.
(Continued)

*Primary Examiner* — Amanda K Hulbert
(74) *Attorney, Agent, or Firm* — Ballard Spahr LLP (57) ABSTRACT

Disclosed is a method. The method may include receiving first data based on a stimulus defined according to a patient. The method may include receiving second data based on the stimulus. The method may include determining an indication of tinnitus. The indication of tinnitus may be based on a comparison between the first data and the second data. The method may include administering a tinnitus treatment on the patient. The treatment may be based on the indication. A tinnitus treatment may include one or more of an biological feedback with the patient, transcranial magnetic stimulation of the patient, surgical insertion of the cochlear implant, the cognitive behavioral therapy, the transcutaneous electrical stimulation, pharmacologic therapy on the patient, or applying a hearing aid to the patient.

27 Claims, 8 Drawing Sheets

(51) Int. Cl.
*A61B 5/12* (2006.01)
*A61N 1/04* (2006.01)

(52) U.S. Cl.
CPC .......... *A61B 5/4836* (2013.01); *A61B 5/7228* (2013.01); *A61B 5/7235* (2013.01); *A61N 1/0456* (2013.01)

(56) References Cited

U.S. PATENT DOCUMENTS

| | | |
|---|---|---|
| 8,353,846 B2 | 1/2013 | Henry et al. |
| 8,870,786 B2 | 10/2014 | Henry et al. |
| 10,537,300 B2 | 1/2020 | Richmond |
| 10,842,418 B2 | 11/2020 | Micheyl |
| 10,959,670 B2 | 3/2021 | Husain et al. |
| 2007/0265683 A1 | 11/2007 | Ehrlich |
| 2009/0292221 A1* | 11/2009 | Viirre .................. A61F 11/00 600/544 |
| 2013/0163797 A1 | 6/2013 | Suzman et al. |
| 2017/0303887 A1 | 10/2017 | Richmond |
| 2019/0167998 A1 | 6/2019 | De Ridder |
| 2019/0201707 A1 | 7/2019 | Stubbeman |
| 2019/0224442 A1 | 7/2019 | Hauptmann et al. |

FOREIGN PATENT DOCUMENTS

| | | |
|---|---|---|
| CN | 104771179 A | 7/2015 |
| CN | 104783808 B | 12/2017 |
| EP | 2942010 A1 | 11/2015 |
| KR | 101666474 B1 | 10/2016 |
| WO | 2006136879 A1 | 12/2006 |
| WO | 2014172814 A1 | 10/2014 |
| WO | 2020018675 A1 | 1/2020 |

OTHER PUBLICATIONS

Ono, M. et al., "Long-Lasting Sound-Evoked Afterdischarge in the Auditory Midbrain," Scientific Reports, 2016, pp. 1-11, vol. 6.
International Search Report and Written Opinion issued in related application No. PCT/US2021/064206 mailed Mar. 11, 2022.

* cited by examiner

TINNITUS TREATMENT AND ANALYSIS

CROSS-REFERENCE TO RELATED APPLICATIONS

This application claims the benefit of U.S. Provisional Application No. 63/127,275, filed Dec. 18, 2020, which is incorporated herein by reference in its entirety.

GOVERNMENT LICENSE RIGHTS

This invention was made with government support under Grant No. W81XWH-18-1-0135 awarded by the U.S. Army Medical Research and Materiel Command and Grant No. DC013822 from the National Institutes of Health. The government has certain rights in the invention.

BACKGROUND

Typically, aural perceptions are detected through the ear and transmitted to the central nervous system. Trauma and other factors may cause aural perceptions without the presence of sound. For example, tinnitus may manifest through signals in the brain or nervous system without external sounds or waves. This subjective tinnitus is distinguished from objective tinnitus—where a sound may be generated in the ear that can be heard or recorded.

SUMMARY

The present disclosure relates to the treatment and analysis of tinnitus and other sensory conditions. It is to be understood that both the following general description and the following detailed description provide only examples and are not restrictive.

Disclosed is a method. The method may include receiving first data based on a stimulus defined according to a patient. The method may include receiving second data based on the stimulus. The method may include determining an indication of tinnitus. The indication of tinnitus may be based on a comparison between the first data and the second data. The method may include administering a tinnitus treatment on the patient. The treatment may be based on the indication. A tinnitus treatment may include one or more of an electrical stimulation of an appendage of the patient, biological feedback with the patient, transcranial magnetic stimulation of the patient, surgical insertion of the cochlear implant, the cognitive behavioral therapy, the transcutaneous electrical stimulation, pharmacologic therapy on the patient, or applying a hearing aid to the patient.

Also disclosed is an apparatus. The apparatus may be or include a system. The apparatus may include one or more processor. The apparatus may include one or more electrode associated with the one or more processor. The electrode may be positioned on a patient. The electrode may be configured to receive potentials based on a stimulus. The apparatus may include one or more non-transitory computer-readable medium. The one or more non-transitory computer-readable medium may include instructions operable upon execution by the one or more processor to determine first data based on the potentials and second data based on the potentials. The instructions may be operable upon execution by the one or more processor to determine an indication of tinnitus based on a comparison between the first data and the second data.

BRIEF DESCRIPTION OF THE DRAWINGS

In order to provide understanding techniques described, the figures provide non-limiting examples in accordance with one or more implementations of the present disclosure, in which.

DETAILED DESCRIPTION

It is understood that when combinations, subsets, interactions, groups, etc. of components are described that, while specific reference of each various individual and collective combinations and permutations of these may not be explicitly described, each is specifically contemplated and described herein. This applies to all parts of this application including, but not limited to, steps in described methods. Thus, if there are a variety of additional steps that may be performed it is understood that each of these additional steps may be performed with any specific configuration or combination of configurations of the described methods.

As will be appreciated by one skilled in the art, hardware, software, or a combination of software and hardware may be implemented. Furthermore, a computer program product on a computer-readable storage medium (e.g., non-transitory) having processor-executable instructions (e.g., computer software) embodied in the storage medium. Any suitable computer-readable storage medium may be utilized including hard disks, CD-ROMs, optical storage devices, magnetic storage devices, memresistors, Non-Volatile Random Access Memory (NVRAM), flash memory, or a combination thereof.

Throughout this application reference is made to block diagrams and flowcharts. It will be understood that each block of the block diagrams and flowcharts, and combinations of blocks in the block diagrams and flowcharts, respectively, may be implemented by processor-executable instructions. These processor-executable instructions may be loaded onto a special purpose computer or other programmable data processing instrument to produce a machine, such that the processor-executable instructions which execute on the computer or other programmable data processing instrument create a device for implementing the functions specified in the flowchart block or blocks.

These processor-executable instructions may also be stored in a computer-readable memory or a computer-readable medium that may direct a computer or other programmable data processing instrument to function in a particular manner, such that the processor-executable instructions stored in the computer-readable memory produce an article of manufacture including processor-executable instructions for implementing the function specified in the flowchart block or blocks. The processor-executable instructions may also be loaded onto a computer or other programmable data processing instrument to cause a series of operational steps to be performed on the computer or other programmable instrument to produce a computer-implemented process such that the processor-executable instructions that execute on the computer or other programmable instrument provide steps for implementing the functions specified in the flowchart block or blocks.

Blocks of the block diagrams and flowcharts support combinations of devices for performing the specified functions, combinations of steps for performing the specified functions and program instruction means for performing the specified functions. It will also be understood that each block of the block diagrams and flowcharts, and combinations of blocks in the block diagrams and flowcharts, may be implemented by special purpose hardware-based computer systems that perform the specified functions or steps, or combinations of special purpose hardware and computer instructions.

Methods and systems are described for using a machine learning classifier(s) for detection and classification. Machine learning (ML) is a subfield of computer science that gives computers the ability to learn through training without being explicitly programmed. Machine learning methods include, but are not limited to, deep-learning techniques, naïve Bayes classifiers, support vector machines, decision trees, neural networks, and the like.

The method steps recited throughout this disclosure may be combined, omitted, rearranged, or otherwise reorganized with any of the figures presented herein and are not intend to be limited to the four corners of each sheet presented.

With little or no objective stimulus, tinnitus is left to patients for identification. For example, tinnitus may be a perception recognized within the brain. This perception may be generated without validation. For example, a medical practitioner may be unable to, equally or otherwise, perceive the tinnitus perceived by the patient with instruments or their own ear. This lack of verification limits the available treatments available to patients with tinnitus at least because its diagnosis is entirely subjective. For example, practitioners may be reluctant or unwilling to perform surgery, electrical stimulation, magnetic stimulation, counseling, pharmacologic therapy, hearing add installation or prescription, or one or more combination thereof. For these reasons, a specific indication for tinnitus coupled with specific treatments based on the specific indication may provide patients necessary relief.

Figure 1:
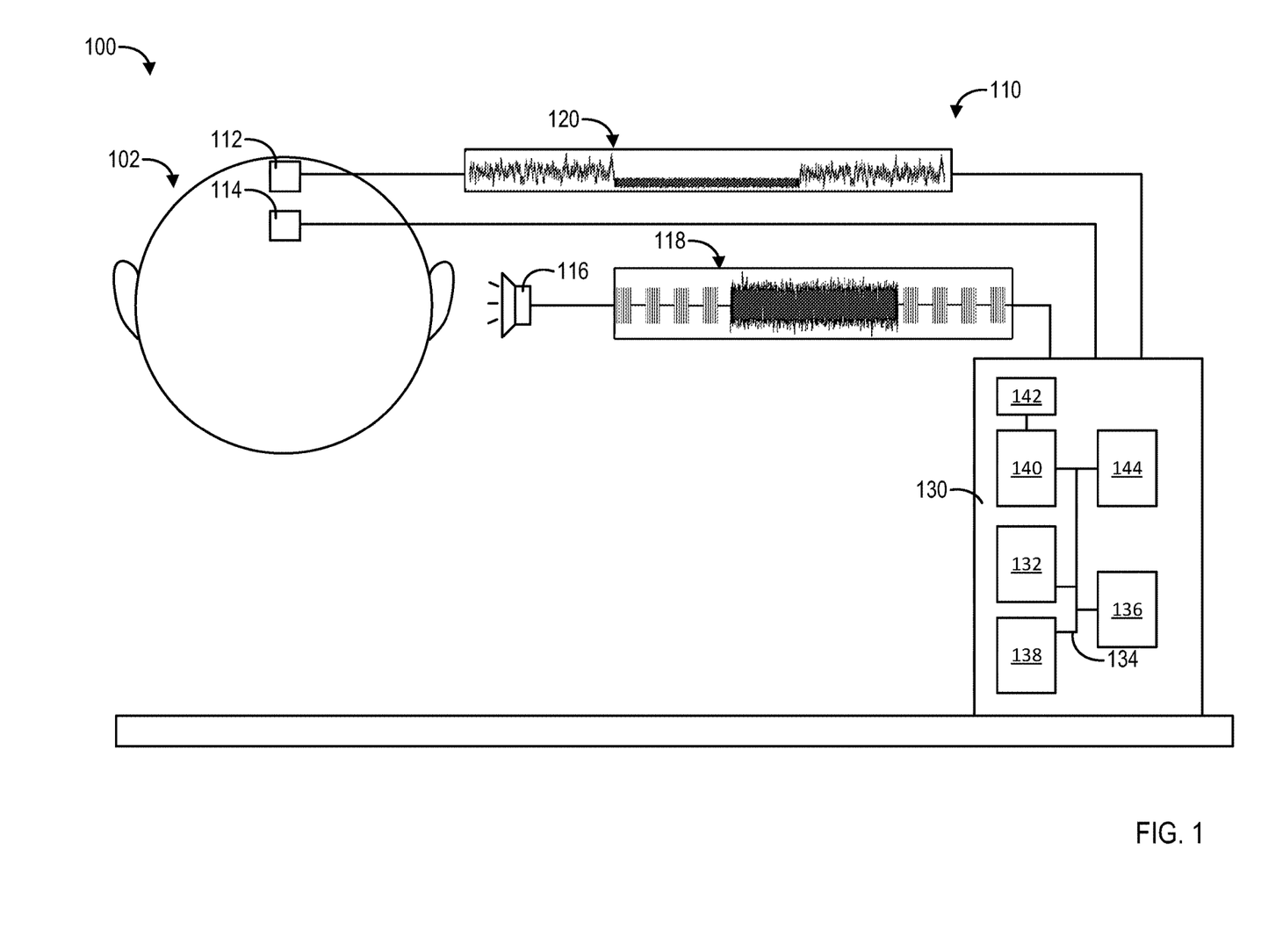
FIG. 1 illustrates an example environment for treating a patient with tinnitus in accordance with one or more implementations of the present disclosure.

Referring to FIG. 1, an example environment 100 for treating a patient 102 with tinnitus in accordance with one or more implementations of the present disclosure is shown. The patient 102 may be subjected to an apparatus 110. The apparatus 110 may be configured to treat tinnitus perceived by patient 102. The apparatus 110 may include one or more electrodes 112, 114 for detecting a response 120 from the patient 102. The response 120 may be based on potentials. The potentials may be various indications. For example, the potentials may be electrical potentials (e.g., voltages) detected within the brain, brain stem, nervous system, or otherwise. The electrodes 112, 114 may be arranged on the patient 102. The electrodes 112, 114 may be configured to provide a positive response, a negative response, a ground, or otherwise. The electrodes 112, 114 may include pads, adhesive or otherwise, for securing an electrical connection between the patient 102 and the apparatus 110. The electrodes 112, 114 may comprise a set for measuring the response 120 and a set for shocking the patient 102 during treatment.

The response 120 may be induced by one or more speakers 116 and stimulus 118. For example, the speaker 116 may produce audible sounds based on the stimulus 118. In some examples, the speaker 116 and stimulus 118 may be collectively referred to as stimulus 118. The stimulus 118 may be defined electrically, aurally, otherwise, or a combination thereof. The stimulus 118 may be generated by circuitry 130. The circuitry 130 may include one or more processor 132 (a processor) connected with one or more non-transitory computer readable medium 138 (a memory). The circuitry 130 may be a microcontroller or otherwise integrated.

The circuitry 130 may be associated with treating a patient 102 in accordance with one or more implementations of the present disclosure. The circuitry may include an amplifier, an analog-to-digital converter 144, or combination thereof for receiving the response 120. The analog-to-digital converter 144 may generate data based on the response 120. For example, the data may be tabular and include timestamps based on the response 120. The data may include potentials determined by the response 120 based on the electrodes 112, 114.

The processor 132 may be configured to receive one or more input from the amplifier, an analog-to-digital converter 144, or combination thereof. The amplifier may amplify the response 120. The amplifier may scale, amplify, or otherwise alter the response 120 into a signal or data useable by processor 132. The data may be one or more dimension based on voltages, currents, or combinations thereof based on the response 120. For example, the data may be an image of the response 120. For example, the voltages or potentials recorded over time may be converted to an image or display format. The data may be defined as pixels or voxels. A processor or a combination of processors may be used to conduct processing on the data. The processor may be a combination of various processing types for general processing and machine learning. For example, the circuitry 130 may include application specific integrated circuits (ASIC), field-programmable gate arrays (FPGA), graphics processing units, central processing units, or combinations thereof. These components may be integrated into the processor 132. The processing of data, by the processor 132 or otherwise, may be distributed across various chasses and infrastructure. For example, the processing may be conducted in the cloud over multiple instances, containers, repositories, or combinations thereof. The data may be stored over multiple instances, containers, repositories or combinations thereof. The computer-readable medium 134 may include instructions. The instructions may be hard-coded or software. For example, the instructions may be defined in a language or code (e.g., machine code, binary data, C, PYTHON, MATLAB). The instructions may be operable upon execution by the processor 132 or otherwise configured to perform operations on the data based on the response 120. The processor 132 may be connected to a display 136 for displaying the indication.

The instructions may be further configured to output commands to a signal generator 140. For example, the instructions may command the signal generator 140 to output the stimulus 118 or components of the stimulus 118. The signal generator 140 may be based on a random number generator or other oscillators (e.g., crystals). The signal generator 140 may be configured to output various pips, chirps, successions, clicks, noise, white noise, other signals, or combinations thereof.

The signal generator 140 may be configured to impart randomness in a signal. For example, the signal generator 140 may be configured to generate a signal having equal intensity at least two frequencies or frequency ranges. As another example, the signal generator 140 may be configured to generate a quantity of randomness. The randomness may be quantified based on various factors. For example, entropy of the data may be calculated based on the frequency, magnitude, phase, combinations thereof, or otherwise. The quantity of randomness may only be comparative having no absolute or explicit meaning other than comparison with other signals or a constant.

The signal generator 140 may output to a filter 142. The filter 142 may be digital or analog. The filter 142 may be a band-pass filter. For example, the filter 142 may be configured by the processor 132 or otherwise to output a signal having a particular band. The band may be defined by a strength of the signal that is greater than a quantity (e.g., greater than −10 dB). The filter 142 may filter the signal from the signal generator 140 to provide the stimulus 118 or portions thereof. For example, the signal generator may be configured to output various pips, chirps, successions, clicks, followed by random noise, and subsequently followed by various pips, chirps, successions, clicks, noise bands, or white noise. The filter 142 may be configured to only filter the white noise and otherwise pass all frequencies.

Figure 2:
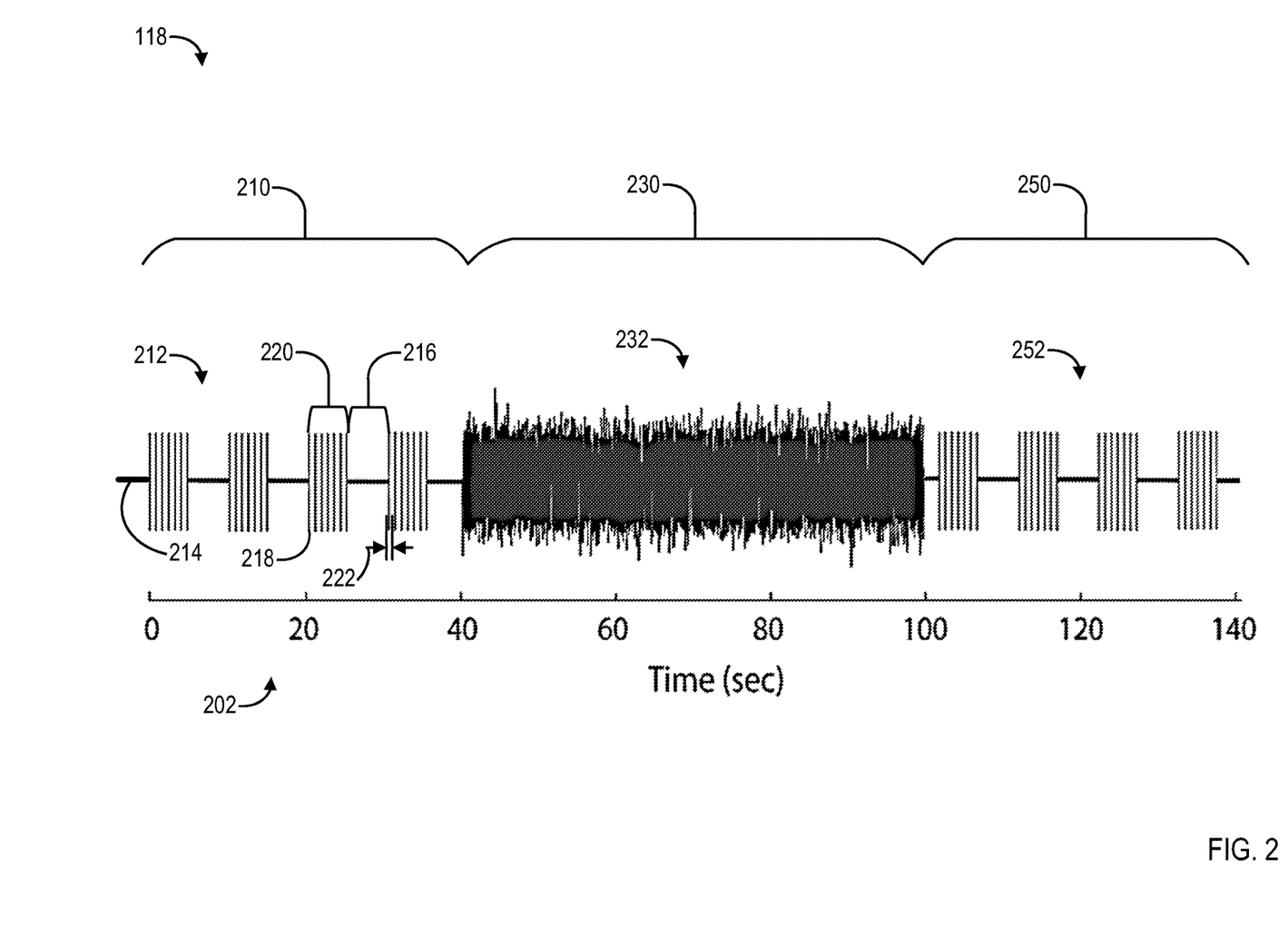
FIG. 2 illustrates an example stimulus associated with treating a patient in accordance with one or more implementations of the present disclosure.

In FIG. 2, an example stimulus 118 associated with treating a patient 102 in accordance with one or more implementations of the present disclosure is shown. The example stimulus 118 may be combined with other components (e.g., pips, chirps, successions, clicks, noise) or segments (e.g., segments 210, 230, 250, 310, 330, 350) discussed throughout this disclosure. Any of the components or segments may be omitted or duplicated.

Figure 8:
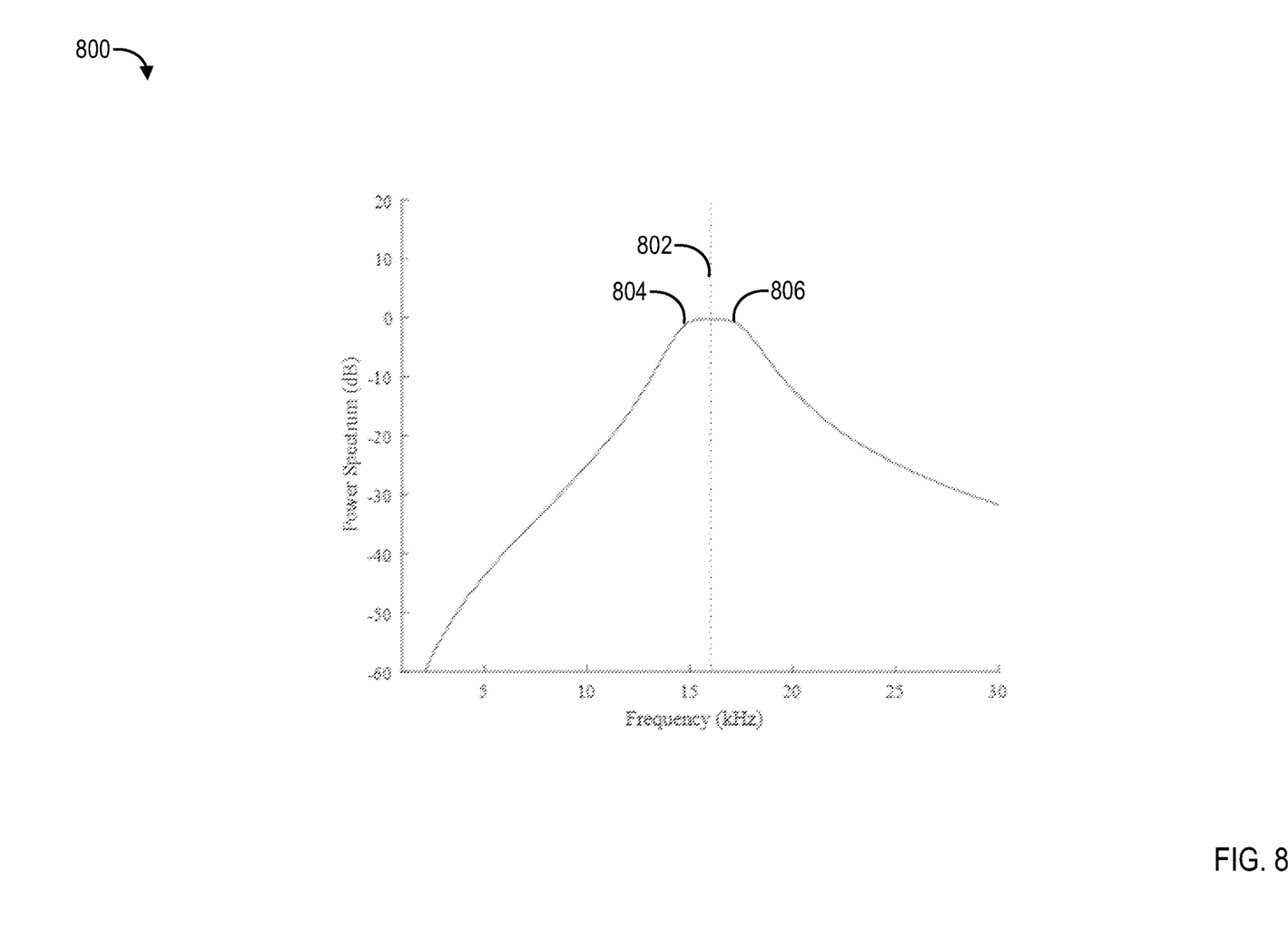
FIG. 8 illustrates an example center frequency in accordance with one or more implementations of the present disclosure.

The stimulus 118 is shown in FIG. 2 as having three segments (e.g., segments 210, 230, 250). More or less segments are contemplated. Segment 210 may be defined by a modulation 212. The modulation 212 may be one or more variations of center signal or center frequency (e.g., center frequency 802 as shown in FIG. 8). For example, the modulation 212 may be defined by pips, chirps, successions, clicks, noise, or periods of inaudibility 216. Modulation 212 and modulation 232 may have different center frequencies. Modulation 212 and modulation 252 may have the same center frequency. As shown, the modulation 212 may include any number of perturbations or lack thereof. For example, the modulation 212 may include an individual perturbation 218 or multiple perturbations that form a succession 220. Succession 220 may be defined by any number of signal parameters. For example, a signal parameter may be a frequency spectrum, a carrier frequency, an amplitude, an amplitude envelope ramp, a presentation rate, a perturbation duration, or combinations thereof. Succession 220 may be defined by a presentation rate, which defines interval between the perturbations 218. The perturbation 218 may be a pressure wave or signal or component that generates the pressure wave. Each perturbation 218 may be based on a pip, chirp, click, or noise (e.g., Gaussian noise).

A pip may be a gated sinusoid of a specified duration. The sinusoid may start or stop at a zero crossing (e.g., zero magnitude). A click may be a brief duration electrical pulse or acoustic pulse (e.g., duration of less than 0.3 ms). A chirp may be a CE-CHIRP. The pip, click, or chirp may be level specific (e.g., audible, inaudible). The chirp may be a frequency-modulated electrical or acoustic signal. A chirp may be configured to compensate for cochlear traveling wave delay. The perturbations may be separated by a period of inaudibility 216. For example, the period of inaudibility 216 may be in between each perturbation 218 or between successions 220. The period of inaudibility 216 may produce sound from the speaker 116 that is inaudible, unperceivable, or undetectable to the patient. For example, the period of inaudibility 216 may distinguish subsequent perturbations 218 or successions 220. The period of inaudibility 216 may be the same duration as a duration of the perturbation 218 or the succession. As another example, the perturbation 218 may be 3 ms and the period of inaudibility 216 may be 44 ms. A perturbation may be defined as a departure from the period of inaudibility or another reference. For example, a departure from zero magnitude 214.

Segment 230 may comprise modulation 232. The modulation 232 may be longer in duration that modulation 212. For example, modulation 232 may be greater than 20 seconds. Modulation 212 may be longer in duration than modulation 232. A duration of the successions 220 may be shorter than the duration of modulation 232. For example, the duration of each of the successions 220 may be less than 20 seconds and the duration of modulation 232 may be longer than 20 seconds. Each of the successions 220 may have the same duration. As an example, each of the successions 220 may have a duration of ten seconds. The period of inaudibility may be ten seconds, and the succession 220 and period of inaudibility may be repeated (e.g., as a cycle) such that modulation 212 or segment 210 is 120 seconds. The duration of modulation 232 may be longer than the duration of an individual succession 220 or a combination of the individual succession 220 (e.g., a cycle duration). For example, the modulation 232 or segment 230 may have a duration of 60 seconds.

The modulation 232 may comprise noise (e.g., Gaussian noise) or tones (e.g., one or more predetermined frequency). The modulation 232 may have a quantity of randomness that is greater than the modulation 212. An indication of entropy may be used to measure the quantity of randomness associated with modulations 212, 232. For example, the quantity of randomness may be calculated based on the frequency, magnitude, phase, combinations thereof, or otherwise. The measurement may be in the time domain, frequency domain, time-frequency domain, or otherwise. The quantity of randomness may only be comparative having no absolute or explicit meaning other than comparison with other signals or a constant. Modulation 232 may occur after modulation 212. Modulation 232 may be filtered (e.g., band-pass filtered) to within a range based on a center frequency. For example, the band-pass filter may limit modulation 232 to within ⅓ octave of the center frequency as shown in FIG. 8. Modulation 232 may be less discontinuous than the period of inaudibility 216. For example, modulation 232 may a continuous signal having a duration of discontinuity less than a duration of the period of inaudibility 216. Modulation 232 may be constant in magnitude or constant in magnitude over a range of frequencies (e.g., between corner frequencies 804, 806). Modulation 232 may comprise more stimulating frequencies than non-stimulating frequencies. For example, the modulation 232 may be characterized by frequencies that stimulate for more than half of a duration of modulation 232 and may exceed 20 seconds.

The center frequency may be determined, set, or defined through pitch matching in the patient or it may also be defined by the practitioner. For example, the center frequency may be determined by generating a sound. The sound may then be adjusted in tone or frequency to that of the perceived tinnitus. For example, the patient may perceive tinnitus at a tone of 3 kHz. The sound may be adjusted until the center frequency is substantially similar to 3 kHz.

The stimulus 118 may include another segment 250. Segment 250 may comprise modulation 252. For example, the modulation 252 may be the same as modulation 212. Modulation 252 may have a duration similar to modulation 212. Modulation 252 may be the opposite of modulation 212. For example, modulation 252 may have a sequence that is ordered in the same way as modulation 212. Modulation 252 may have a sequence that is in reverse order from modulation 212. Modulation 252 may have the same duration as modulation 212, as shown over time 202.

Figure 3:
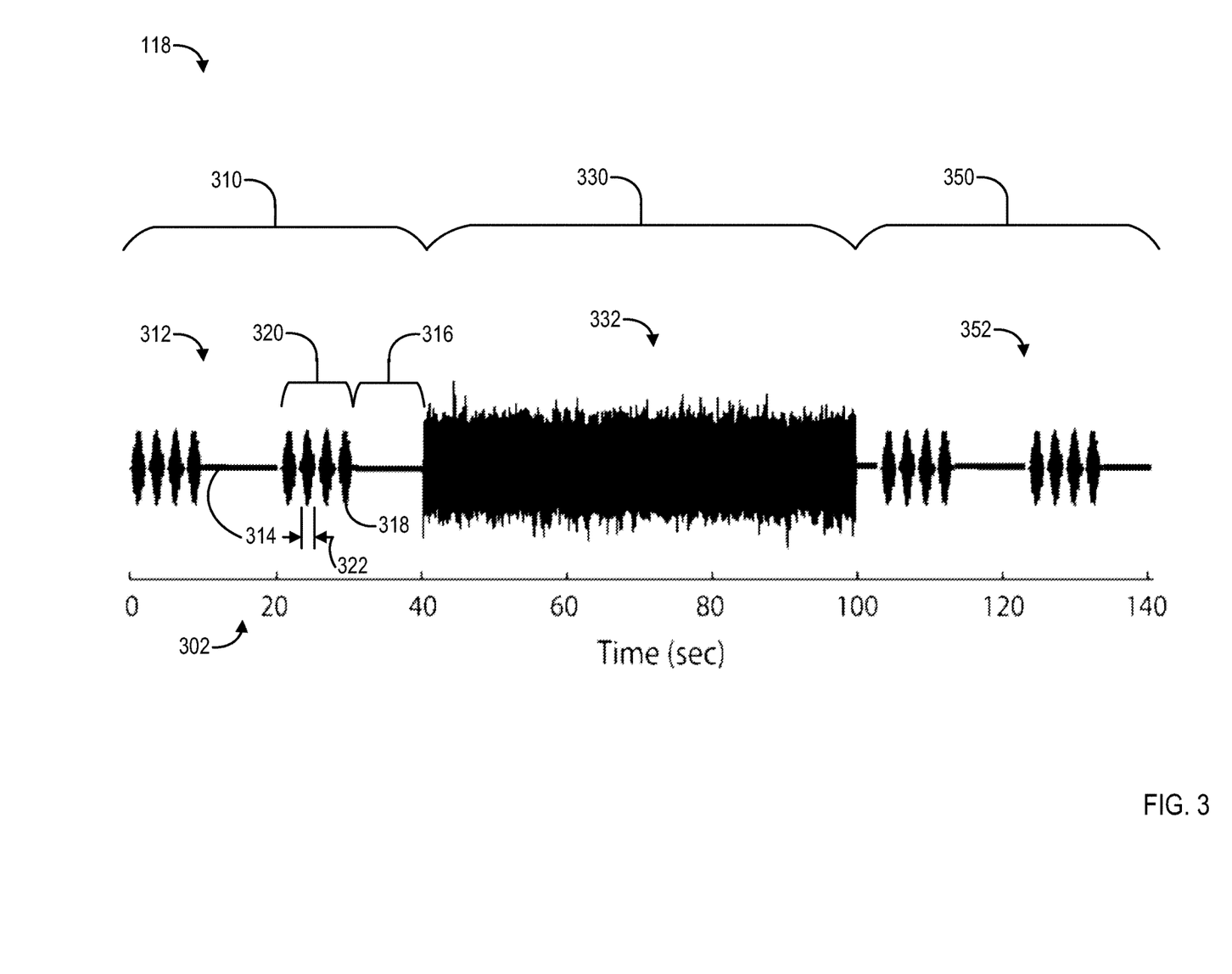
FIG. 3 illustrates an example stimulus associated with treating a patient in accordance with one or more implementations of the present disclosure.

In FIG. 3, an example stimulus 118 associated with treating a patient 102 in accordance with one or more implementations of the present disclosure is shown. The example stimulus 118 may be combined with other components (e.g., amplitude-modulated waveform) or segments (e.g., segments 210, 230, 250, 310, 330, 350) discussed throughout this disclosure. Any of the components or segments may be omitted or duplicated.

The stimulus 118 is shown in FIG. 3 as having three segments (e.g., segments 310, 330, 350). More or less segments are contemplated. Segment 310 may be defined by a modulation 312. Modulation 312 may comprise any or all of the characteristics of modulation 212. The modulation 312 may be one or more variations of a center frequency. For example, the modulation 312 may be defined by an amplitude-modulated waveform or periods of inaudibility 316. As shown, the modulation 312 may include any number of perturbations or lack thereof. For example, the modulation 312 may include an individual perturbation 318 or multiple perturbations that form a succession 320. The succession 320 may be based on a tone, frequency, or otherwise. Each perturbation 318 may be based on a waveform. The perturbations may be separated by a period of inaudibility 316. For example, the period of inaudibility 316 may be in between each perturbation 318 or between successions 320. For example, the period of inaudibility 316 may distinguish subsequent perturbations 318 or successions 320. The period of inaudibility 316 may be the same duration as a duration of the perturbation 318 or the succession. A perturbation may be defined as a departure from the period of inaudibility or another reference. For example, a departure from zero magnitude 314.

Segment 330 may comprise modulation 332. Modulation 332 may comprise any or all of the characteristics of modulation 232. The modulation 332 may comprise noise. For example, the modulation 332 may have a quantity of randomness that is greater than the modulation 312. An indication of entropy may be used to measure the quantity of randomness associated with modulations 312, 332. For example, the quantity of randomness may be calculated based on the frequency, magnitude, phase, combinations thereof, or otherwise. The measurement may be in the time domain, frequency domain, time-frequency domain, or otherwise. The quantity of randomness may only be comparative having no absolute or explicit meaning other than comparison with other signals, a constant, or a reference. Modulation 332 may occur after modulation 312. The stimulus 118 may include another segment 350. Segment 350 may comprise modulation 352. Modulation 352 may comprise any or all of the characteristics of modulation 252. For example, the modulation 352 may be the same as modulation 312. Modulation 352 may be the opposite of modulation 312. For example, modulation 352 may have a sequence that is ordered in the same way as modulation 312. Modulation 352 may have a sequence that is in reverse order from modulation 312. Modulation 352 may have the same duration as modulation 312, as shown over time 302.

The stimulus 118 may define or be associated with a window (e.g., one or more of windows 222, 322). The window 222, 322 may be based on the presentation rate, which defines interval between the perturbations 218. For example, the window 222, 322 may be sized to capture the response 120 by the patient 102 based on each perturbation 218 of stimulus 118 and a period of inaudibility there between.

Figure 4:
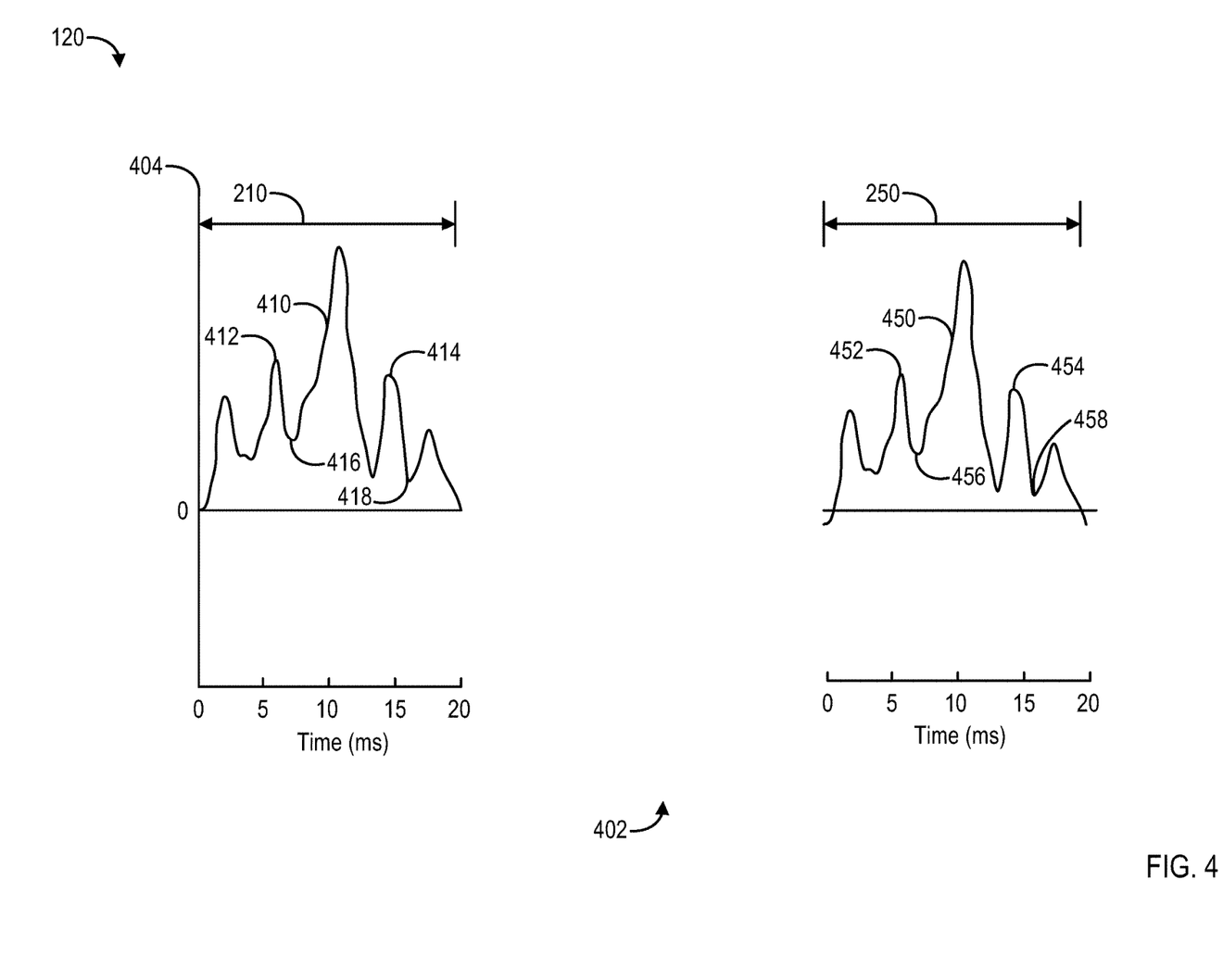
FIG. 4 illustrates an example response in accordance with one or more implementations of the present disclosure.

Referring to FIG. 4, an example response 120 in accordance with one or more implementations of the present disclosure is shown. The response 120 may include portions based on the segments 210, 230, 250, 310, 330, 350. For example, the response 120 may include a portion that defines data 410. The data 410 may be based on potentials defined by the patient 102 according to stimulus 118. The data 410 may in the time domain, frequency domain, time-frequency domain, or otherwise. As shown, the data 410 may be an average of the response 120 according to the window (e.g., window 222, 322) for segment 210. For example, data 410 may be an average of each window 222 or slice of the response 120, indicating an average of the auditory response from each of the perturbations 218 of the stimulus 118. The data 410 may include peaks 412, 414 and troughs 416, 418. The peaks 412, 414 and troughs 416, 418 may be defined by the related segment 210 of the stimulus 118. For example, the data 410 may be associated with the same duration as the segment 210 of the stimulus. The data 410 may be delayed (e.g., stimulus at 1 ms may correspond to response at 2 ms). The data 410 may be indicated on a voltage or potential scale 404 over time 402.

The response 120 may include a portion that defines data 450. The data 450 may be based on potentials defined by the patient 102 according to stimulus 118. The data 450 may in the time domain, frequency domain, time-frequency domain, or otherwise. As shown, the data 450 may be an average of the response 120 according to the window (e.g., window 222, 322) for segment 250. For example, data 450 may be an average of each window 222 or slice of the response 120, indicating an average of the auditory response from each of the perturbations 218 of the stimulus 118. The data 450 may include peaks 452, 454 and troughs 456, 458. The peaks 452, 454 and troughs 456, 458 may be defined by the related segment 210 of the stimulus 118. For example, the data 450 may be associated with the same duration as the segment 210 of the stimulus. The data 450 may be delayed. The data 450 may be indicated on a voltage or potential scale 404 over time 402. For example, the data 450 may include both positive and negative potentials that contain peaks 452, 454 and troughs 456, 458. The peaks 452, 454 and troughs 456, 458 may be defined by the related to 218 in segment 250 of the stimulus 118. For example, the data 450 may be averaged with the repetition rate. The data 450 may be indicated on a voltage or potential scale 404 over time 402

Data 410, 450 may be based on two separate responses. For example, data 410 may be based on a response with a center frequency (e.g., center frequency 802 of FIG. 8) at a predetermined value (e.g., 1 kHz), and also based on a response with a center frequency near the frequency of tinnitus perceived by the patient 102 (e.g., 3 kHz). Data from each of the responses pertaining to the segment (e.g., segment 210) may be combined for comparison discussed herein. For example, data from each of the responses may be averaged or statistically selected (e.g., maximum value, minimum value for a dataframe). In ways discussed herein, the average response for perturbations 218 of the segment 210 may be compared with the average response for perturbations 218 of the segment 250, the average responses for perturbations 218 of the segment 210 at one center frequency may be compared with the average response for perturbations 218 of the segment 210 at another center frequency, or combinations thereof.

Figure 5:
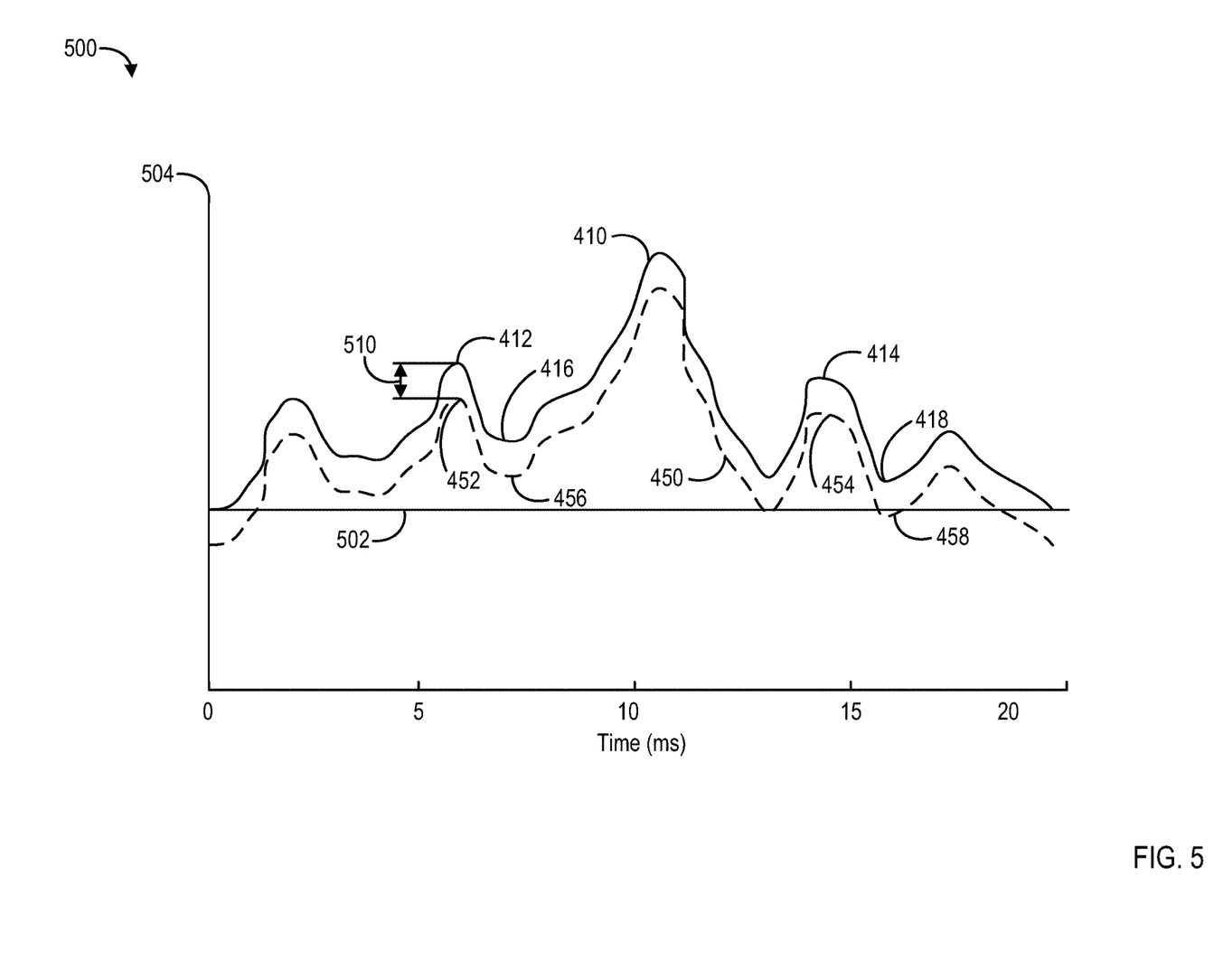
FIG. 5 illustrates an example characteristic identification in accordance with one or more implementations of the present disclosure.

In FIG. 5, an example characteristic identification 500 in accordance with one or more implementations of the present disclosure is shown. Various characteristics are contemplated. The comparisons may be measured on the entire waveforms or on averaged waveforms at predetermined points based on the data 410, 450. For example, the characteristic may be a difference or absolute difference in magnitude, phase, frequency, voltage, potential, or otherwise. The characteristic may be a distance between peaks, a distance between a peak and a trough, an elapsed time, a spectral measure, variation determined by bootstrapping, a statistical measure, a rate of change, a change over time, or combinations thereof. The difference may be measured at predetermined points or based on the data 410, 450. Characteristic identification may be performed with a comparison.

For example, a comparison (e.g., comparison 510) may be made to compare data 410 with data 450. The comparison may be indicative of a difference in magnitude between peaks 412, 452 of the respective data 410, 450, and provide an estimate or indication of underlying tinnitus although not directly related to any natural phenomena therein. For example, such comparison may not be related to any actual sounds or perceptions of the patient 102 only a measurement of characteristics that may be indicative of underlying disease. That is, the comparison or characteristic may not be based on the actual perception of tinnitus and only electrical signals or potentials from the brainstem that may or may not be related to the actual perception.

The comparison may be related to a threshold, quantity, or value to provide an indication of underlying disease severity and subsequent treatment or remedial measures. For example, the comparison may result in a numerical value. This numerical value may be compared with a quantity or value that is used to approximate an indication of tinnitus. The comparison may be based on an alignment of the data 410, 450 on axes 502, 504 where 502 is time-relative and 504 is magnitude, frequency, or phase relative.

The amplitude of the peaks 412, 414, 452, 454, troughs 416, 418, 456, 458, and peak to trough distances may be compared. For example, the data 410 may be compared to data 450 by subtracting data 450 from data 410. Data 410, 450 may be normalized. For example, as shown in Equation 1, an indication may be defined. For example, all of the values in data 410 may be subtracted from all of the values in data 450 and divided by the sum of all of the values in data 410 and all of the values in data 450.

Data 410, 450 may be tested for the presence of a response to the modulation frequency of the stimulus 118. The coherence and the strength of the signal within data 410, 450 may be compared to that of other modulation frequencies of the stimulus 118. If the response to the modulation frequency is greater than the response to other modulation frequencies, tinnitus within the patient may be indicated.

Bootstrapping may be applied to any of the data discussed herein to compare data (e.g., data 410) with data (e.g., data 450). For example, random samples may be taken from data associated with segment 210, 310 (e.g., data 410) and compared with random samples of data from segment 250, 350 (e.g., data 450). Similarity between the averaged responses may be computed to determine a correlation coefficient. The process may be repeated until a comparison equal to the correlation between data is generated. The comparison identified by the bootstrap or otherwise may be indicative of tinnitus when compared with a threshold, value, or quantity.

Figure 6:
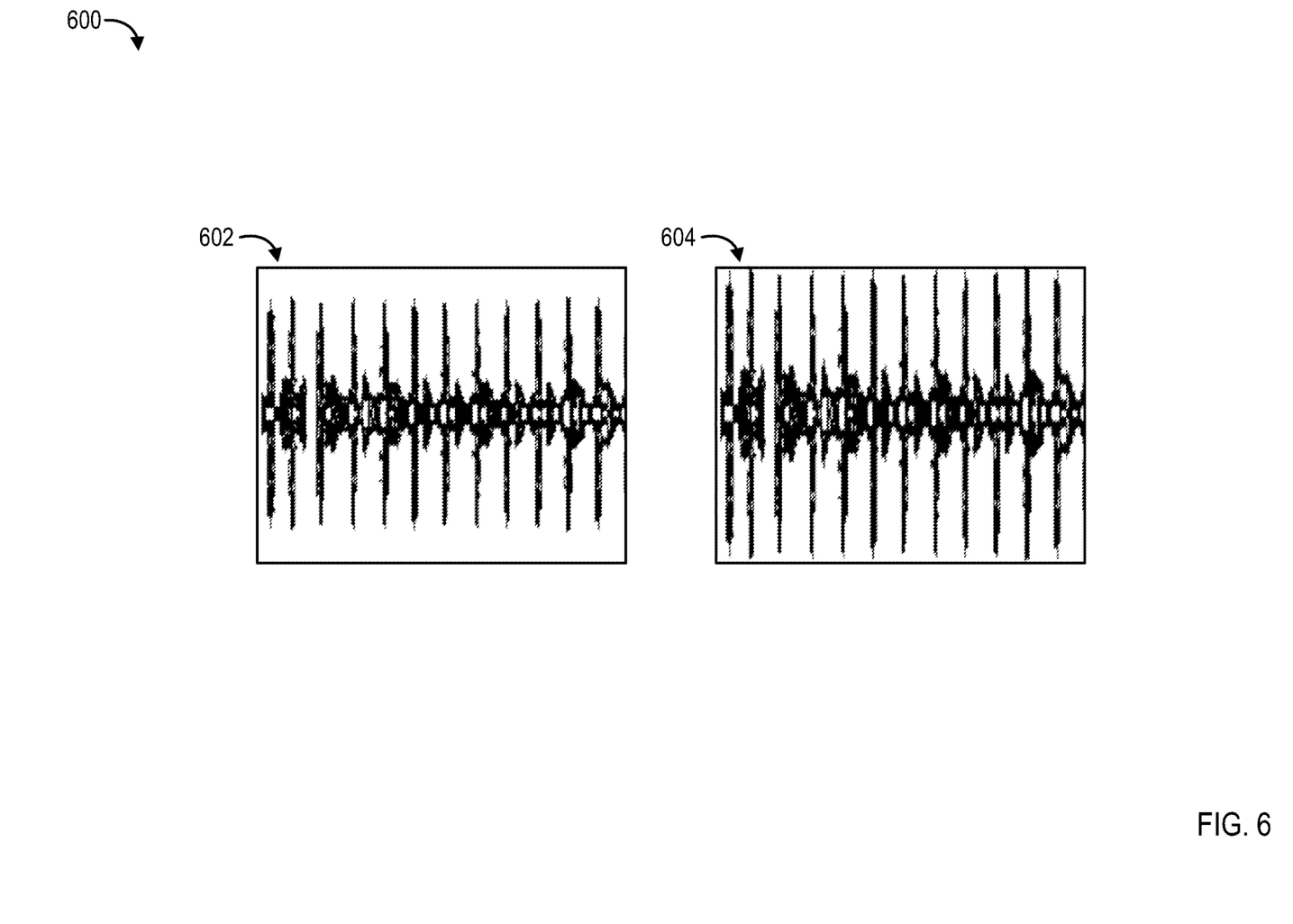
FIG. 6 illustrates example time-frequency data in accordance with one or more implementations of the present disclosure.

In FIG. 6, example time-frequency data 600 in accordance with one or more implementations of the present disclosure is shown. The time-frequency data 602, 604 may be based on the response 120. For example, the time-frequency data 602 may be based on segment 210 or segment 310 and time-frequency data 604 may be based on segment 250 or segment 350. A series of steps may be used to identify characteristics between time-frequency data 602 and time-frequency data 604. For example, convolutions may be used to identify distances or differences between the time-frequency data 602 and time-frequency data 604. A pixel-wise difference between the time-frequency data 602 and the time-frequency data 604 may be used to compare the time-frequency data 602 and the time-frequency data 604. For example, each pixel or groups of pixels of time-frequency data 602 may be subtracted from similarly located pixels to identify a difference. The average of all the differences may equate to a comparison.

Figure 7:
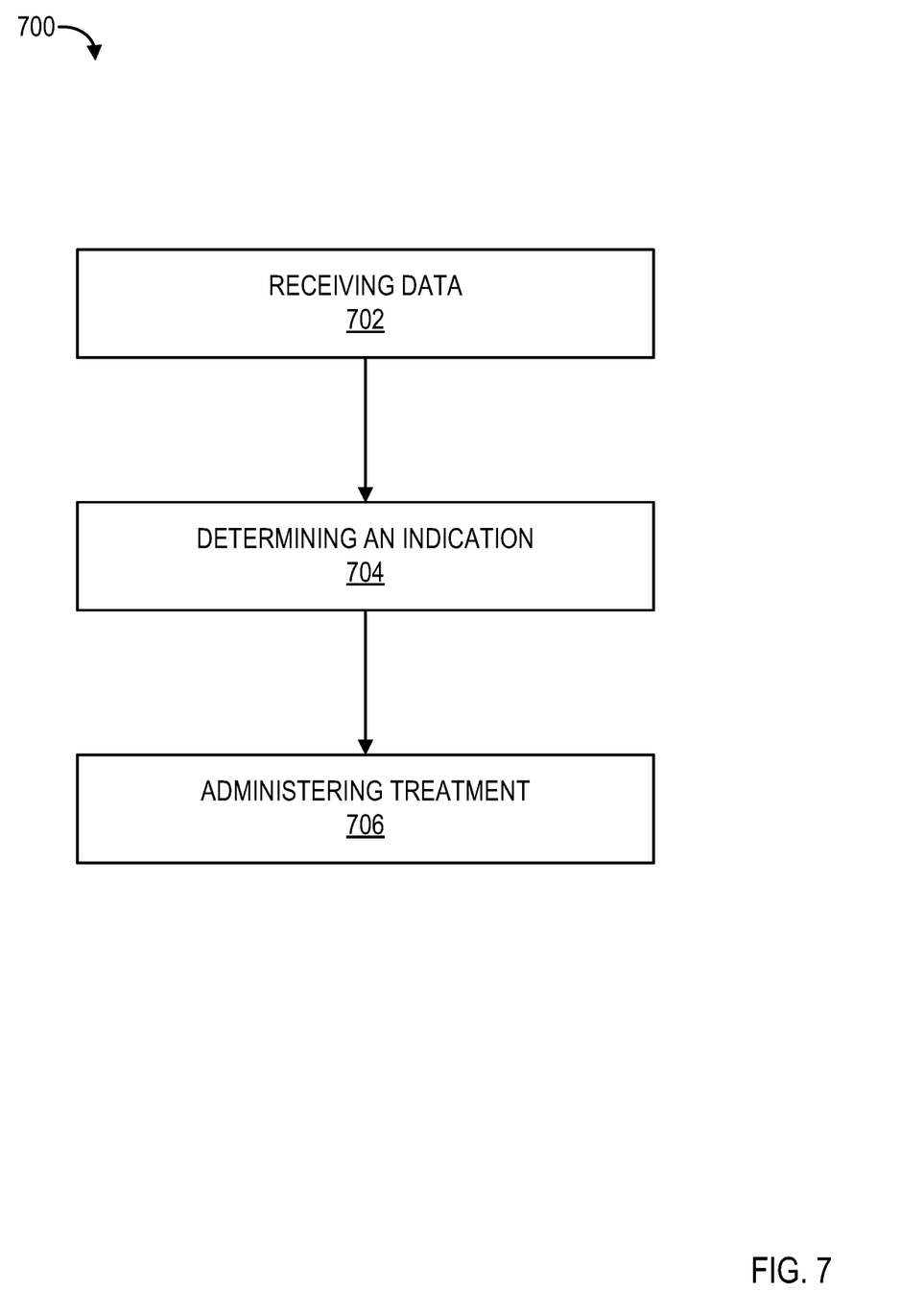
FIG. 7 illustrates an example method for treating a patient in accordance with one or more implementations of the present disclosure.

In FIG. 7, an example method 700 for treating a patient in accordance with one or more implementations of the present disclosure is shown. Any of the components discussed throughout this disclosure may be used to perform the steps stated herein. The steps may be omitted, rearranged, or duplicated. In step 702, the data is received. For example, one or more of data 410, 450, 602, 604 may be received. The data 410, 450, 602, 604 may be represented in tabular form. For example, magnitudes may be represented with timestamps. Data 410, 450, 602, 604 may be represented in a pictorial form. Data 410, 450, 602, 604 may be stored within the non-transitory computer-readable medium 134 or elsewhere and defined based on the response 120 according to analog-to-digital converter 144. In step 704, an indication may be determined. The indication may be an estimation of tinnitus. For example, the indication may be a percentage of likelihood that the patient 102 is experiencing a perception of tinnitus. The indication may provide a severity of the tinnitus based on the likelihood. The indication may also be categorical. The determination may be based on a comparison of data. For example, data 410, 450, 602, 604 may be compared to determine the indication.

In step 706, a treatment may be administered based on the indication. Treatments may be applied based on the category or likelihood determined. For example, the tinnitus treatment may include electrical stimulation of an appendage of the patient. The circuitry 130 and electrodes 112, 114 or other circuitry and other electrodes may apply the electrical stimulation. The electrical stimulation may be non-ablative and non-intrusive. Treatment may further include surgical insertion of a cochlear implant based on the indication, application of cognitive behavioral therapy and transcutaneous electrical stimulation.

The magnitude of electrical stimulation may be based on the likelihood or category. For example, higher likelihoods may warrant higher ranges of electrical stimulation. Other treatments are contemplated. For example, biological feedback with the patient 102, transcranial magnetic stimulation of the patient 102, pharmacologic therapy on the patient 102, applying a hearing aid to the patient 102, electrical stimulation of the tongue, or transcutaneous stimulation of the head or body. After application of the treatment or portions thereof, steps 702, 704 may be repeated to determine efficacy of the treatment. For example, after a hearing aid or pharmacologic is applied, the stimulus 118 may be applied to the patient to determine whether the treatment is successful (e.g., reduces or eliminates tinnitus).

In such circumstances, the choice and magnitude of therapy may be based on the likelihood or category of tinnitus. For example, a high likelihood of tinnitus may direct programming of the hearing aid for higher output or higher output at a determined tinnitus frequency.

In FIG. 8, an example frequency domain 800 in accordance with one or more implementations of the present disclosure is shown. The frequency domain 800 may be depicted in accordance with the stimulus 118, modulations 212, 232, 252 or portions thereof. The center frequency 802 may be based on one or more of the stimulus 118, modulations 212, 232, 252 or portions thereof. For example, the center frequency 802 may be based on modulation 212 without the portions that are inaudible. The center frequency 802 may be frequency that is within the audible range of a patient (e.g., 20 Hz-100 kHz for animals, 20 Hz-20 kHz for humans). The perturbations 218, 318 may be based on the center frequency 802. The center frequency 802 may be defined based on corner frequencies 804, 806 of the frequency power spectrum. As an example, the center frequency 802 may be equidistant from the corner frequencies 804, 806. The center frequency 802 may also be a geometric mean of the stimulus 118, modulations 212, 232, 252 or portions thereof.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered with only a true scope and spirit being indicated by the following claims.

What is claimed is:

1. A method comprising:
generating a first stimulus comprising a first center frequency and a second stimulus comprising a second center frequency, wherein each of the first stimulus and the second stimulus comprises at least one of a tone pip, a chirp, a narrow-band noise, or a click, and wherein the second center frequency is determined based on a patient-perceived tinnitus frequency;
receiving first data based on the first stimulus;
receiving second data based on the second stimulus;
determining an indication of tinnitus including at least one of a determined severity or a determined likelihood of tinnitus based on a comparison between the first data and the second data in a time-frequency domain; and
administering a tinnitus treatment on a patient based on the determined severity or likelihood of tinnitus, the tinnitus treatment comprising transcutaneous electrical stimulation, biological feedback with the patient, transcranial magnetic stimulation of the patient, surgical insertion of a cochlear implant, a cognitive behavioral therapy, pharmacologic therapy on the patient, applying a hearing aid to the patient, or any combination thereof, wherein at least one parameter of the tinnitus treatment is configured according to the indication of tinnitus.

2. The method of claim 1, wherein the first stimulus further comprises a first segment and a second segment, the first segment comprising a first modulation defining a succession, the succession having a first duration and the second segment comprising a second modulation having a second duration longer than the first duration.

3. The method of claim 2, wherein the first modulation is characterized by a first quantity of randomness and the second modulation is characterized by a second quantity of randomness greater than the first quantity of randomness.

4. The method of claim 2, wherein the second modulation is generated by steps comprising:
generating Gaussian noise; and
filtering the Gaussian noise within a range according to a center frequency.

5. The method of claim 4, further comprising:
generating sound based on the first stimulus; and
adjusting a frequency of the sound until the frequency of the sound is substantially similar to a frequency of tinnitus perceived by the patient.

6. The method of claim 4, wherein the first modulation is defined by a sequence, the sequence comprising the succession and a period of inaudibility.

7. The method of claim 6, wherein the succession comprises pulses of a same perturbation and a duration of the period of inaudibility and a duration of the succession are substantially equal.

8. The method of claim 6, wherein the succession comprises an amplitude-modulated waveform and a duration of the period of inaudibility and the first duration are substantially equal.

9. The method of claim 2, wherein the first modulation comprises a sinusoid.

10. The method of claim 2, wherein the first stimulus comprises a third segment, the third segment comprising the first modulation.

11. The method of claim 10, wherein the first data is based on the first segment and the second data is based on the third segment.

12. The method of claim 10, wherein the first data is based on the first segment and the second data is based on the first segment.

13. The method of claim 1, wherein the first data and the second data are based on a response of the patient to at least one of the first stimulus or the second stimulus in the time-frequency domain and the comparison is indicative of differences between the first data in the time-frequency domain and the second data in the time-frequency domain.

14. The method of claim 1, wherein the first data and the second data are based on a response of the patient to at least one of the first stimulus or the second stimulus and the comparison is based on an average of correlations of random samples of the first data and an average of correlations of random samples of the second data.

15. The method of claim 1, wherein the first data and the second data are based on a response of the patient to at least one of the first stimulus or the second stimulus and the comparison based on a characteristic of the first data in a time domain and a characteristic of the second data in the time domain.

16. The method of claim 15, wherein the characteristic of the first data is a peak of the first data and the characteristic of the second data is a peak of the second data.

17. The method of claim 15, wherein the characteristic of the first data is a trough of the first data and the characteristic of the second data is a trough of the second data.

18. The method of claim 16, wherein the characteristic of the first data is a distance of the first data and the characteristic of the second data is a distance of the second data.

19. The method of claim 1, wherein the indication is a likelihood of tinnitus.

20. The method of claim 1, wherein the indication is categorizes the tinnitus.

21. The method of claim 1, wherein each of the first stimulus and the second stimulus is configured to evoke a response in a brainstem of the patient, the response expressed by potentials.

22. The method of claim 1, further comprising:
measuring potentials based on each of the first stimulus and the second stimulus to define the first data and the second data.

23. The method of claim 1, wherein:
generating the first stimulus having the first center frequency and the second stimulus having the second center frequency is performed by a processor;
receiving the first data based on the first stimulus further comprises receiving, via one or more electrodes, the first data based on the first stimulus;
receiving the second data based on the second stimulus further comprises receiving, via the one or more electrodes, the second data based on the second stimulus; and
determining the indication of tinnitus is performed by the processor.

24. A method comprising:
generating a first stimulus comprising a first center frequency and a second stimulus comprising a second center frequency, wherein each of the first stimulus and the second stimulus comprises at least one of a tone pip, a chirp, a narrow-band noise, or a click, and wherein the second center frequency is determined based on a patient-perceived tinnitus frequency;
receiving first data based on the first stimulus, the first data based on a first response of a patient to the first stimulus in a time-frequency domain;
receiving second data based on the second stimulus, the second data based on a second response of the patient to the second stimulus in the time-frequency domain;
determining an indication of tinnitus including at least one of a determined severity or a determined likelihood of tinnitus based on a comparison between the first data and the second data, the comparison indicative of differences between the first data in the time-frequency domain and the second data in the time-frequency domain; and
administering a tinnitus treatment on the patient based on the determined severity or likelihood of tinnitus, the tinnitus treatment comprising transcutaneous electrical stimulation, biological feedback with the patient, transcranial magnetic stimulation of the patient, surgical insertion of a cochlear implant, a cognitive behavioral therapy, pharmacologic therapy on the patient, applying a hearing aid to the patient, or any combination thereof, wherein at least one parameter of the tinnitus treatment is configured according to the indication of tinnitus.

25. A method comprising:
generating a first stimulus comprising a first center frequency and a second stimulus comprising a second center frequency, wherein each of the first stimulus and the second stimulus comprises at least one of a tone pip, a chirp, a narrow-band noise, or a click, and wherein the second center frequency is determined based on a patient-perceived tinnitus frequency;
receiving first data based on the first stimulus, the first data based on a first response of a patient to the first stimulus in a time-frequency domain;
receiving second data based on the second stimulus, the second data based on a second response of the patient to the second stimulus in the time-frequency domain;
determining an indication of tinnitus including at least one of a determined severity or a determined likelihood of tinnitus based on a comparison between the first data and the second data, the comparison based on an average of correlations of random samples of the first data and an average of correlations of random samples of the second data; and
administering a tinnitus treatment on the patient based on the determined severity or likelihood of tinnitus, the tinnitus treatment comprising transcutaneous electrical stimulation, biological feedback with the patient, transcranial magnetic stimulation of the patient, surgical insertion of a cochlear implant, a cognitive behavioral therapy, pharmacologic therapy on the patient, applying a hearing aid to the patient, or any combination thereof, wherein at least one parameter of the tinnitus treatment is configured according to the indication of tinnitus.

26. A method comprising:
receiving first data based on a stimulus, wherein the stimulus comprises a first segment, the first segment comprises a first modulation defining a succession, the succession having a first duration, and the first modulation comprises a tone pip, a chirp, a narrow-band noise, or a click;
receiving second data based on the stimulus;
determining an indication of tinnitus based on a comparison between the first data and the second data, the indication comprising a category of tinnitus affecting a patient at one or more frequencies; and
administering a tinnitus treatment on the patient based on the indication of tinnitus, the tinnitus treatment comprising:
providing a magnitude of transcutaneous electrical stimulation, where the magnitude is based on the category of tinnitus;
applying a hearing aid to the patient, the hearing aid being configured to provide higher output at the one or more frequencies based on the category of tinnitus; or
one or more combination thereof.

27. The method of claim 26, wherein:
receiving the first data based on the stimulus further comprises receiving, via one or more electrodes, the first data based on the stimulus;
receiving the second data based on the stimulus further comprises receiving, via the one or more electrodes, the second data based on the stimulus; and
determining the indication of tinnitus is performed by a processor.

\* \* \* \* \*